United States Patent [19]

Jackisch

[11] 4,376,221

[45] * Mar. 8, 1983

[54] STABILIZATION OF DIBROMOSTYRENE

[76] Inventor: Philip F. Jackisch, 4218 Rosewold, Royal Oak, Mich. 48073

[*] Notice: The portion of the term of this patent subsequent to Aug. 10, 1999, has been disclaimed.

[21] Appl. No.: 130,185

[22] Filed: Mar. 13, 1980

[51] Int. Cl.$^3$ .................. C07C 14/42; C09K 15/18
[52] U.S. Cl. .................................. 570/103; 252/1; 252/401; 570/111
[58] Field of Search .................. 252/1, 401; 570/111, 570/103

[56] References Cited

U.S. PATENT DOCUMENTS 2,451,642 10/1948 Watson ........................... 252/401 X
2,965,565 12/1960 McDonald ..................... 252/401 X
3,546,125 12/1970 Archer et al. ..................... 570/111

FOREIGN PATENT DOCUMENTS 1230979 5/1971 United Kingdom ............... 570/105

OTHER PUBLICATIONS

Kirk-Othmer Encyclopedia, vol. 11, pp. 410-412 (1953).
Kirk-Othmer Encyclopedia, vol. 2, p. 741 (1978).
Kirk-Othmer Encyclopedia, vol. 3, pp. 128-147 (1978).

Primary Examiner—Richard D. Lovering
Attorney, Agent, or Firm—Donald L. Johnson; Joseph D. Odenweller; John F. Hunt

[57] ABSTRACT

Dibromostyrene is stabilized against unwanted polymerization by incorporating therein a stabilizing amount of a phenylene diamine such as N,N,N',N'-tetramethylphenylene-p-diamine or N,N'-diethylphenylene-p-diamine.

4 Claims, 1 Drawing Figure

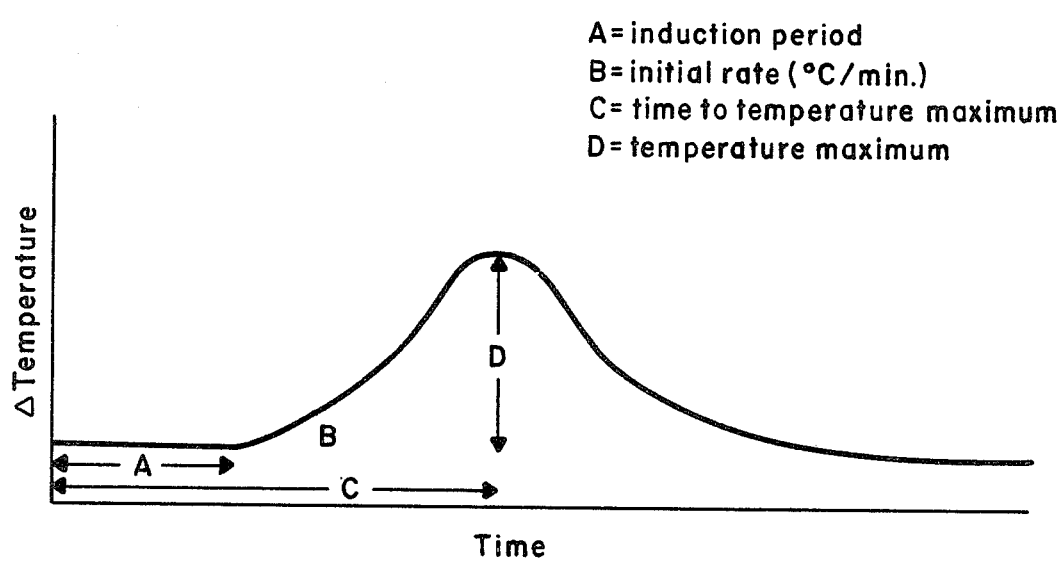
Representative Differential Thermal Analysis Curve of Polymerization

STABILIZATION OF DIBROMOSTYRENE

BACKGROUND OF THE INVENTION

Dibromostyrene, which has been suggested as a flame retardant monomer, has a considerable tendency to undergo polymerization during storage. This polymerization tendency is greater than with styrene itself. It has been suggested in British Pat. No. 1,230,979, that dibromostyrene be stabilized with picric acid or a mixture of picric acid, and (i) a quinone such as hydroquinone or benzoquinone or (ii) a phenol such as tert-butyl-catechol.

SUMMARY OF THE INVENTION

This invention comprises the discovery that undesired polymerization of dibromostyrene during storage is reduced if the dibromostyrene is intimately mixed with a lower alkyl phenylene diamine wherein the alkyl group(s) are from one to about five carbon atoms. Hence, this invention comprises as a composition of matter, dibromostyrene containing a stabilizer amount of a compound having the formula

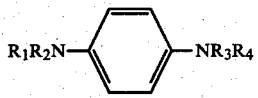

wherein each R is alike or different and is selected from the class consisting of hydrogen and lower alkyl groups of up to about five carbon atoms.

Two preferred compounds of the above formula are N,N,N',N'-tetramethyl-p-phenylene diamine and N,N'-diethylphenylene-p-diamine.

DESCRIPTION OF THE DRAWING

The drawing shows a representation of a differential thermal analysis (DTA) curve obtained when the polymerization of dibromostyrene with an inhibit or is followed by DTA using the apparatus and procedure described herein. As shown, the value for (A) indicates how long the induction period before the polymerization ensues, while the value for (C) indicates the time for the polymerization to reach its maximum. The slope of the curve at (B) after the terminus of (A) is an indication of the polymerization rate, while the height of (C) gives the temperature maximum reached.

Without a polymerization inhibitor, the period indicated by (A) is non-existent or very short. With a polymerization retardant, it makes the slope of the line at (B) less steep and diminishes the height of (D). The average polymerization rate in °C. per unit time can be calculated from the slope of the line connecting the end of (A) with the maximum of the curve; i.e. where the curve is intercepted by the height (D).

DESCRIPTION OF PREFERRED EMBODIMENTS

This invention works well when applied to dibromostyrene made by dehydrohalogenation such as dehydrobromination of a 2-bromoethyldibromobenzene. A preferred method for the dehydrobromination is that described in my copending application entitled "Preparation of Dibromostyrene" and filed concurrently with this application. It is not critical that this invention be applied to dibromostyrene made in the manner disclosed in that application. The invention also gives better results when the dibromostyrene contains less than about 0.1 weight percent of β-bromoethyldibromobenzene impurity and less than about 2 weight percent of tribromostyrene impurity. However, the tribromostyrene level may be 8-9 percent or higher. Dibromostyrene preparations usually are largely 2,4-dibromostyrene, or 3,4-dibromostyrene or a mixture thereof.

The object of the invention is to stabilize the unwanted polymerization of dibromostyrene which can occur upon storage. Thus, the process of this invention is the stabilization of dibromostyrene at ordinary storage temperatures, usually no more than about 35°-38° C. For testing, the temperature to which the dibromostyrene and stabilizer system are exposed can be much higher to accelerate obtaining the test results.

The stabilizers of this invention have the nucleus

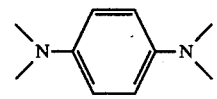

wherein the unsatisfied valences are bonded to radicals which do not unduly hinder the ability of the stabilization activity to take place. A skilled practitioner using the test procedure described in the Example can readily determine if a compound having the above depicted nucleus is an additive of this invention. If use of the test described in the Example shows that the compound under investigation gives a longer induction period than that determined for the untreated dibromostyrene, then the compound under investigation is an additive or stabilizer of this invention.

The unsatisfied valences, in the formula of the active nucleus depicted above, can be bonded to hydrogen or typically, a hydrocarbyl group. Preferably, the hydrocarbyl group is rather small and not of such complexity as to either make the compound economically unattractive or unduly low in reactivity on a weight of additive basis. Further, as shown in the example below, good activity can be obtained with a compound of simple structure. Hence, unless there is a gain in cost-effectiveness or other useful property or characteristic, then there may not be an advantage in substituting a more heavily substituted phenylene diamine for the lower alkyl substituted products wherein each radical bonded to nitrogen (and not the phenylene nucleus) is hydrogen or an alkyl group of one to five; more preferably, one or two carbons.

The good results shown below with p-phenylene diamines suggests that the other diamines, viz, the ortho and meta isomers of the above-described additives can also be used as stabilizers for dibromostyrene.

The stabilizers of this invention are preferably used in a concentration of from about 20 to about 2000 ppm, more preferably from about 100 to about 600 ppm.

EXAMPLE 1

A differential thermal analysis apparatus was constructed to measure the heat of polymerization of stored monomer samples. Two thermopiles were constructed (originally with 6 thermocouples each but more recently with 5) with iron-Constantin junctions. Sample containers consisted of 18 ml wide-mouthed bottles with caps drilled with a hole through which was fitted a piece of glass tubing sealed at the bottom end to form a thermowell. The glass tubes were 8 mm in outside diameter and 90 mm long and were filled with 5 drops of Dow Corning No. 200 Silicone Oil to help in heat transfer. The thermopiles were inserted into the thermowells of two cells, one containing an inert fluid (originally m-dibromobenzene but more recently Dow Corning No. 200 Silicone Oil), and the other approximately 15 g (9 ml) of dibromostyrene or an equal volume of bromostyrene or styrene. The sample and reference cells were placed in a wooden holder in a Blue M, Stabil-Therm Poweromatic 70 oven. The oven temperature was measured with a Doric Trendicator 400 A type K/°C. digital pyrometer connected to a thermocouple with its end in the wooden cell holder. The temperature differential between the reference cell and the monomer-containing cell was recorded on a Houston Instruments OmniScribe recorder at either 1 millivolt or 10 millivolts full scale (equal to 4.8 or 48 degrees C.).

The dibromostyrene used in the test contained 1.1 weight percent monobromostyrene and 8.7 percent tribromostyrene.

Results of the testing were as follows:

| Inhibitor | Induction Period | Initial Poly.Rate | Average Poly.Rate | Time of Max. Rate | Temp. Max. |
|---|---|---|---|---|---|
| None | 0 | 3.8°hr | 4.4°hr. | 1.5 hr | 6.3° C. |
| 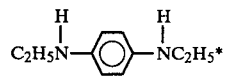* | 33.6 | 0.17 | 0.52 | 38.4 | 2.5° C. |
| * | 45.0 | 1.15 | 0.80 | 46.9 | 1.5° C. |

*400 ppm

The above results suggest the use of the aforesaid compounds wherein $R_1, R_2, R_3,$ and $R_4$ are depicted above are independently selected from hydrogen and lower alkyl groups of up to about five carbon atoms, such a compound being employed in an amount ranging from about 20 to about 2000 ppm, more preferably from about 100 to about 600 ppm.

I claim:

1. As a composition of matter, dibromostyrene containing a stabilizer amount of a polymerization inhibitor compound having the formula

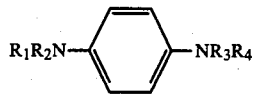

wherein each R is alike or different and is selected from the class consisting of hydrogen and lower alkyl groups of up to about five carbon atoms.

2. A composition of claim 1 wherein the amount of said stabilizer is from about 20 to about 2000 ppm.

3. A composition of claim 2 wherein said compound is N,N'-diethyl-p-phenylene diamine.

4. A composition of claim 2 wherein said compound is N,N,N', N'-tetramethyl-p-phenylene diamine.

* * * * *

UNITED STATES PATENT AND TRADEMARK OFFICE
CERTIFICATE OF CORRECTION

PATENT NO. : 4,376,221
DATED : March 8, 1983
INVENTOR(S) : Philip F. Jackisch

It is certified that error appears in the above-identified patent and that said Letters Patent is hereby corrected as shown below:

On the title page Insert

--(73) Assignee: Ethyl Corporation,
            Richmond, Virginia --

Signed and Sealed this

Seventeenth Day of July 1984

[SEAL]

Attest:

GERALD J. MOSSINGHOFF

Attesting Officer

Commissioner of Patents and Trademarks